US006090088A

United States Patent [19]

Nichols

[11] Patent Number: 6,090,088

[45] Date of Patent: Jul. 18, 2000

[54] ARTIFICIAL INSEMINATION SYSTEM WITH VALVE ASSEMBLY

[76] Inventor: Lew O. Nichols, 1519 James St., Webster City, Iowa 50595

[21] Appl. No.: 09/243,567

[22] Filed: Feb. 3, 1999

[51] Int. Cl.$^{7}$ .................. A61F 5/44

[52] U.S. Cl. .................. 604/347; 604/349; 119/838

[58] Field of Search .................. 604/346, 347, 604/349, 350; 119/838

[56] References Cited

U.S. PATENT DOCUMENTS 4,744,352 5/1988 Emery .

*Primary Examiner*—John D. Yasko
*Attorney, Agent, or Firm*—Chase & Yakimo, L.C.

[57] ABSTRACT

A phantom mare includes a housing having inlet and outlet ends with a bore therebetween. A bladder surrounds the bore. Upon injection of a warmed fluid into the housing, the fluid is captured between the bladder and bore surface to distend and warm the bladder. Upon stallion penetration in the outlet end the discharged semen is directed to a collection container at the outlet end. A valve assembly regulates a user discharge of the fluid from the housing so that the distended bladder returns to a non-distended position to preclude irritation on the stallion upon withdrawal. The removal of heat of the discharged fluid from the housing reduces the possibility of damage to the deposited semen.

16 Claims, 2 Drawing Sheets

ARTIFICIAL INSEMINATION SYSTEM WITH VALVE ASSEMBLY

BACKGROUND OF THE INVENTION

This invention relates to a semen collection device and, more particularly, to an improved collection device having a user operable valve assembly thereon for enhancing the volume and quality of semen collected thereby.

The collection of semen from a stallion utilizing a phantom mare is known. One such device is as shown in U.S. Pat. No. 4,744,352 to Emery, which is incorporated by reference herein. Emery shows the utilization of a phantom mare having an artificial vagina in the form of a cylinder, with the cylinder having a first end for stallion penetration and a second in communication with a semen collection container. Upon insertion of the stallion's reproductive member into the cylinder and subsequent semen release, the semen is directed to the collection container. The cylinder includes a rubber bladder about the interior wall of the cylinder. A fill spout in the exterior cylinder wall allows for injection of water warmed to a desired temperature into the cylinder for capture between the rubber bladder and the cylinder wall. This structure is said to simulate the vagina of a mare. After semen release the water within the cylinder is released upon stallion withdrawal to allow the user to open the fill spout.

One problem with the use of this past design is that upon withdrawal of the stallion from the cylinder, the distended bladder is bearing on portions of the tumescent (Docket 2642) reproductive member. This pressure irritates the stallion. Also, a suction is created which can cause an undesirable migration of a portion of the discharged semen towards the inlet end of the cylinder upon stallion withdrawal. Furthermore, the stallion should be removed from the phantom to allow the user safe access to the fill spout. As such, the semen within the cylinder is subject to a prolonged heat exchange with heat from the warmed bladder. This prolonged exchange may, if not kill the sperm, degrade the quality thereof. Thus, it is desirable to eliminate these problems found in prior phantom mare devices.

In response thereto I have invented a phantom mare system which quickly and safely releases the fluid from the cylinder. A valve assembly is mounted about an exhaust port on the underside of the cylinder to control release of the warmed water therefrom. The valve assembly is user operated by a cord extending between the valve assembly and the handler positioned beyond the phantom. Thus, the handler need not approach the underside of the phantom. Upon opening the valve assembly the water is quickly released from the cylinder. This release diminishes the fluid pressure on the bladder allowing for an easier and quicker withdrawal of the tumescent stallion from the cylinder without an accompanying stallion irritation and migration of semen towards the inlet end of the cylinder. Moreover, the quick release of the warmed water diminishes the period of heat transfer with the discharged semen. Accordingly, the valve assembly not only enhances the quantity of the semen but also the quality thereof.

It is therefor a general object of the invention to provide an improved semen collection device with valve assembly which enhances the quantity and quality of the collected semen.

Another object of this invention is to provide a device, as aforesaid, which utilizes a user-controlled valve assembly to regulate the safe discharge of a heat exchange fluid from the device.

A further object of the invention is to provide a device, as aforesaid, which allows the user to operate the device in the presence of the stallion.

A still further object of the invention is to provide a device, as aforesaid, which quickly and efficiently removes the fluid therefrom which allows quicker withdrawal of the stallion from the device and/or reduces the time of heat exchange with the sperm collected therein.

Other objects and advantages of this invention will become apparent from the following description taken in connection with the accompanying drawings, wherein is set forth by way of illustration and example, a now preferred embodiment of this invention.

DESCRIPTION OF THE PREFERRED EMBODIMENT

Figure 1:
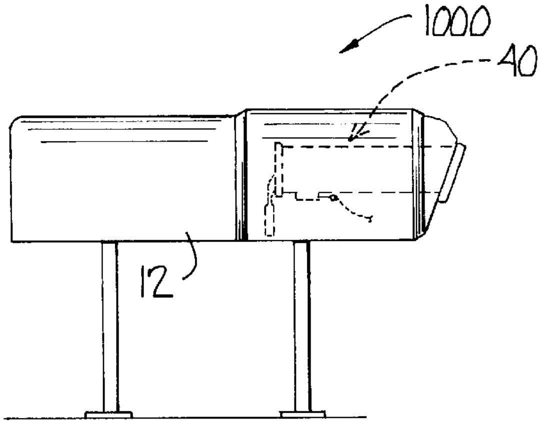
FIG. 1 diagrammatically shows a phantom collection device with the artificial device shown in phantom lines.

Turning more particularly to the drawings, FIG. 1 diagonally shows a phantom 1000 having the artificial vagina 40 therein with a collection container 52 attached thereto. As herein noted the non-primed numbers are intended to correspond to similar elements in the incorporated Emery U.S. Pat. No. 4,744,352. Primed numbers are utilized in connection with applicant's invention.

Figure 2:
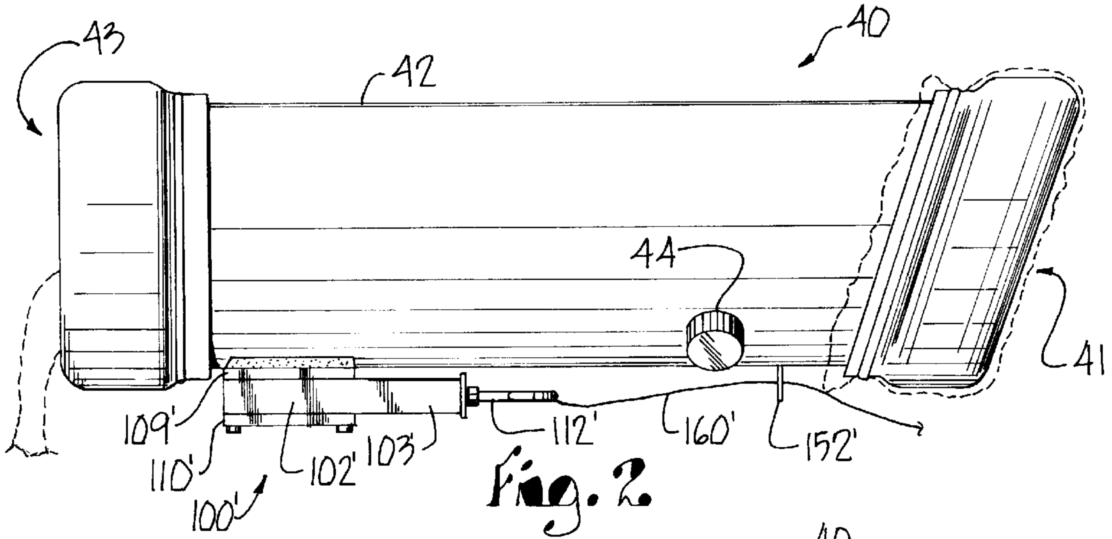
FIG. 2 is a view, on an enlarged scale, of the artificial vagina removed from the collection device.
Figure 3:
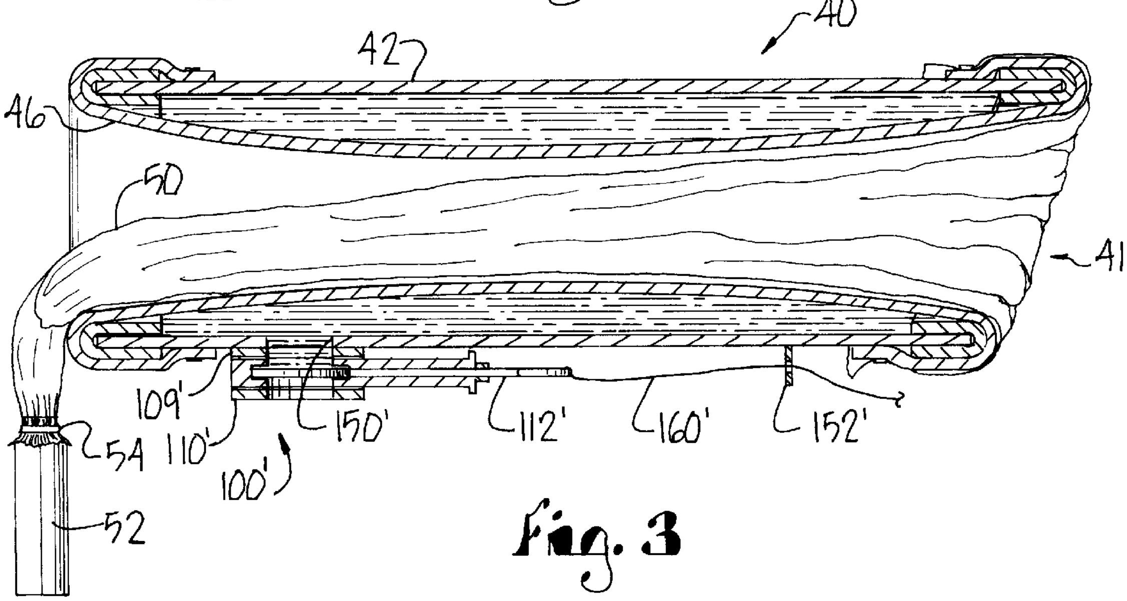
FIG. 3 is a sectional view of the FIG. 2 device taken along the longitudinal centerline thereof.
Figure 4:
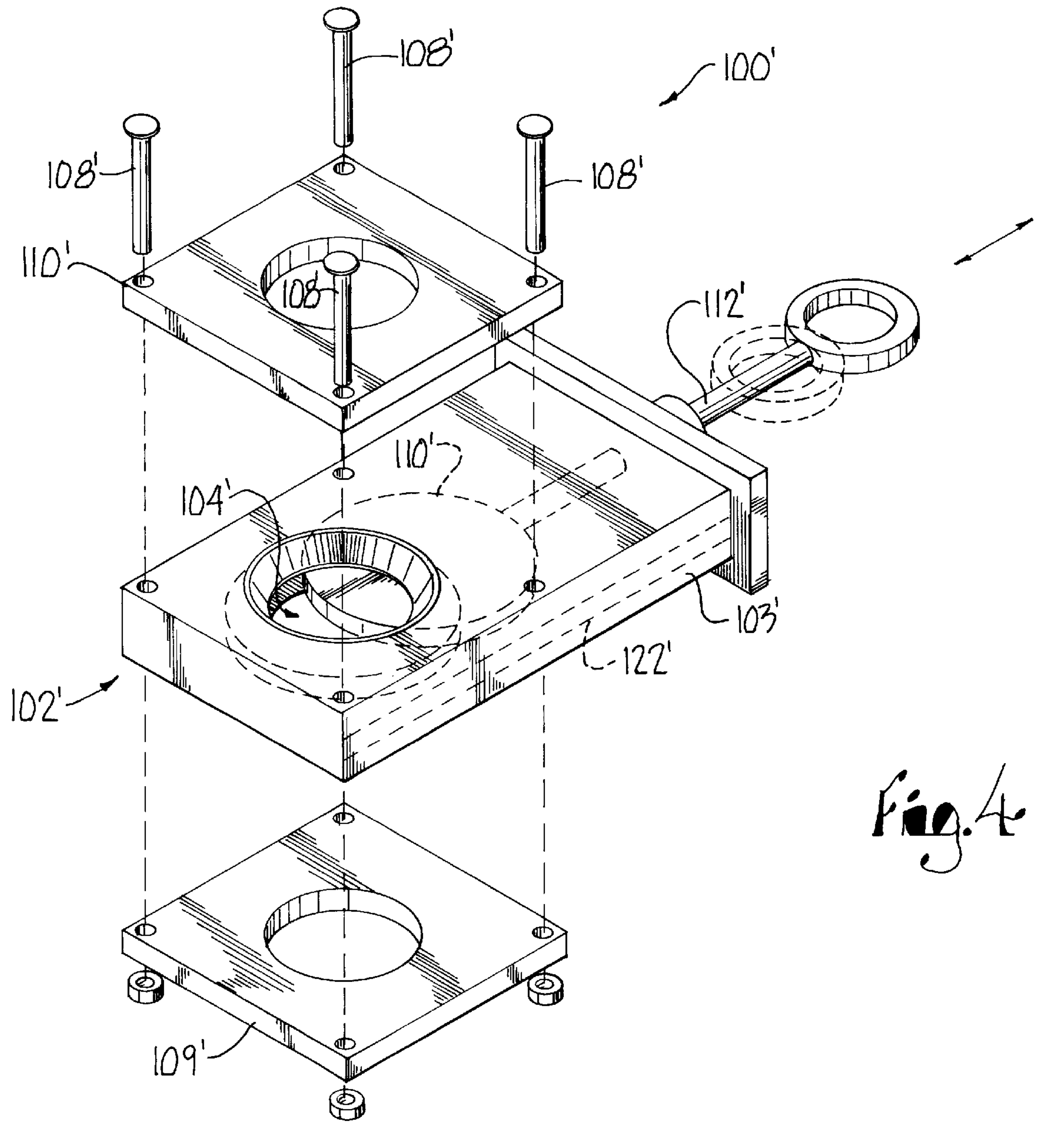
FIG. 4 is an exploded view of the valve assembly on an enlarged scale.

FIG. 2 shows the artificial vagina device 40 (hereinafter "the device") on an enlarged scale as removed from the phantom with FIG. 3 showing the device in a sectional view along the longitudinal centerline thereof. As such, the device includes a cylinder 42 having an open-ended rubber liner 46 or jacket. The ends of the bladder 46 are secured about the inlet 41 and outlet ends 43 of the cylinder 42. A fill cap 44 allows for insertion of fluid within the cylinder such that it is captured between the interior surface of the cylinder wall and the bladder 46. The captured fluid distends the bladder 46 from a position away from the interior wall of the cylinder and provides for heat transfer to the bladder 46 and the bore of the cylinder 42.

Also, as best shown in FIG. 3, is a condom-like plastic bag 50 which is attached about the inlet end 41 of the cylinder. The bag 50 extends through the jacketed cylinder 42 with the open distal end of the plastic bag 50 being attached to a collection bottle 52 by clamp 54. The device 40 is placed within the body section 12 and adjusted for the stallion. Upon entry of the stallion into the inlet end 41 of the cylinder 42, the distended bladder 46 presses against the stallion so as to provide a sensation of entering a mare. Heretofore after semen discharge the tumescent stallion is withdrawn from the device 40. However, the distended bladder 46 bears against the stallion's member and caused irritation thereto. Moreover, a suction was created within the cylinder 42 such that a portion of the discharged sperm would migrate to the inlet end 41 instead of the collection container 52.

I have addressed these problems by providing a valve assembly 100' which regulates the discharge of the fluid from an exhaust port 150' in the underside of the cylinder 42. The valve assembly 100' includes a valve housing 102' which has an interior bore 104' therein. The housing 102' is attached to the underside of the cylinder 42 by bolts 108' or the like extending through apertures in mounting plates 109', 110'. Upon such attachment, the bore 104' registers with the port 150' in the cylinder 42. Within the housing 102' is a valve body 110' and a valve rod 112' extending therefrom.

The primary housing 102' includes a housing portion 103' which houses a portion of the valve rod 112' and valve body 110' therein when the valve body 110' is at an open position. Extending along both sides of the valve housings are slots 122' which provide a race for the edges of the valve body 110'. Accordingly, the valve body 110' is slidable between a first position which closes the bore 104' and a second position which opens the bore 104'. Extending from the valve rod 112' is a cord 160' which is threaded through a grommet 152' on the underside of the cylinder 42. The cord 160' is long enough such that the cord 160' can be grasped by a user standing outside the phantom device.

In use, the fill port 44 is opened. Warmed water is injected into the cylinder 42 such that the fluid is captured between the interior surface of the cylinder 42 bore and the bladder 46. Accordingly, the distended bladder 46 reduces the diameter of the cylinder 42 bore. At this point the valve body 110' is at a closed position which precludes escape of the fluid from the exhaust port 150'. After stallion discharge, the user pulls on the cord 160' such that the cord tension moves the valve 110' to its second open position. At the open position, the fluid is quickly discharged from the open exhaust port 150'. This reduces fluid pressure on the bladder 46 so that the tumescent stallion can be withdrawn from the cylinder 42 without irritation. Moreover, no suction is created within the cylinder 42 upon withdrawal. Thus, the discharged semen will not migrate away from the collection container 52. Furthermore, the exhaust of the heated fluid from the cylinder 42 ceases the heat transfer of this fluid to the bladder 46, cylinder 42 bore and semen therein. Accordingly, as the period of heat transfer is diminished, the probability of sperm deterioration due to such heat exchange is precluded. Thus irritation to the stallion is diminished and the likelihood of an enhanced quantity and/or quality of the discharged sperm is increased.

Although a now preferred embodiment of my invention has been illustrated and described herein, it is not to be limited thereto, except by set forth in the following claims and allowable functionally equivalents thereof.

Having thus described the invention, what is claimed as new and desired to be secured by Letters Patent is as follows:

1. In an animal semen collection structure having an artificial vagina in the form of a housing having a bore bounded by inlet and outlet ends, a bladder about an interior of the housing, a port for the injection of a fluid between the housing and the bladder, the improvement comprising:

an exhaust port extending between an interior and exterior of said housing, said exhaust port in communication with the fluid in the housing;

means for regulating a flow of the fluid from said exhaust port, said regulating means having a first position for closing said exhaust port precluding a fluid discharge from said exhaust port and a second open position allowing a fluid discharge through said exhaust port;

means for control of said regulating means, a flow of the fluid from said exhaust port reducing pressure of the fluid on the bladder and a heat transfer of the fluid thereto.

2. An animal semen collection structure as claimed in claim 1 wherein said regulating means comprises:

a valve having a configuration designed to close said exhaust port, said valve positioned in extension across said exhaust port at said first position and positioned beyond said exhaust port at said second position.

3. An animal semen collection structure as claimed in claim 2 wherein said control means comprises:

means extending from said valve for moving said valve between said first and second positions.

4. An animal semen collection structure as claimed in claim 3 wherein said moving means comprises a rod extending from said valve.

5. An animal semen collection structure as claimed in claim 4 further comprising a cord attached to said rod, a tension on said cord moving said valve between said first and second positions.

6. An animal semen collection structures as claimed in claim 5 wherein said cord is of a length for a user grasping of a portion of said cord positioned beyond said structure.

7. An animal semen collection structure as claimed in claim 1 wherein said regulating means comprises:

a valve housing;

a bore within said valve housing;

means for attaching said valve housing to said housing to register said valve housing bore with said exhaust port;

a valve body in said housing;

means for moving said valve body between a first position across said valve housing bore to preclude fluid flow therethrough and a second position without said valve housing bore to allow a fluid therethrough.

8. An animal semen collection structure as claimed in claim 7 wherein said moving means comprises:

a valve stem having a first end connected to said valve body and a second end beyond said valve housing, a manipulation of said valve stem moving said valve body between said first and second positions.

9. An animal semen collection structure as claimed in claim 1 wherein said regulating means comprises:

valve means connected to said exhaust port for said regulating of said fluid flow through said exhaust port, said valve means having a first position for obstructing said exhaust port and a second position free of said exhaust port.

10. A phantom female device for use in an artificial semen collection system comprising:

a body section adapted to represent a female animal;

a housing in said body section adapted to represent a vagina of the female animal, said housing including:

an inlet end for penetration of the male animal reproductive member;

an outlet end for discharge of deposited semen therefrom;

an interior bore of said housing communicating said inlet and outlet ends;

a bladder in said housing extending about said bore;

a port in said housing for entry of a fluid therein at a desired temperature, said fluid captured between said bladder and said housing for interaction with said bladder;

means on said housing for regulating a flow of said fluid therethrough, said means including an exhaust port in said housing in communication with said fluid, said means having a closed position and an open position, said open position for discharge of the fluid in said housing;

means for moving said regulating means from said closed to said open position for discharge of said fluid from said exhaust port.

11. The device as claimed in claim 10 wherein said regulating means comprises:

a valve body extending across said exhaust port in said closed position, said moving means displacing said valve body to a position outside said exhaust port.

12. The device as claimed in claim 11 wherein said moving means comprises:

means extending from said valve body for a purchase thereon, whereby to move said valve body to said open position.

13. The device as claimed in claim 10 wherein said regulating means comprises:

a valve body extending across said exhaust port in said closed position, said moving means moving said valve body to a position outside said exhaust port.

14. The device as claimed in claim 10 further comprising a container in communication with said outlet end for collecting deposited semen therein.

15. A phantom female device for use in an artificial semen collection system comprising:

a body section;

a housing in said body section adapted to present a vagina of a female animal, said housing including:

an inlet for penetration of a reproductive member of a male animal therein;

a distal outlet for flow of discharged semen thereto;

a bore in said housing communicating said inlet and outlet;

a flexible wall extending about an interior surface of said housing and said bore;

means in said housing for insertion of a fluid between said flexible wall and said housing for displacing said bladder from said interior surface;

a collection container in communication with said distal outlet of said housing;

valve means on said housing having an open position for releasing said fluid from said housing;

means for user movement of said valve means from a closed position to said open position.

16. The collection system as claimed in claim 15 wherein said valve means comprises:

an exhaust port in said housing in communication with said fluid;

a valve body extending across said exhaust port in said closed position, said movement means moving said valve body to a position beyond said exhaust port.

* * * * *